(12) United States Patent
Sugahara et al.

(10) Patent No.: US 6,530,907 B1
(45) Date of Patent: Mar. 11, 2003

(54) CHANNEL SWITCHING APPARATUS

(75) Inventors: Atsushi Sugahara, Osaka (JP); Tetsuya Yamamoto, Osaka (JP); Michihiko Matsushima, Osaka (JP)

(73) Assignee: Sugan Co., Ltd., Osaka (JP)

( * ) Notice: Subject to any disclaimer, the term of this patent is extended or adjusted under 35 U.S.C. 154(b) by 0 days.

(21) Appl. No.: 09/720,653

(22) PCT Filed: Aug. 5, 1998

(86) PCT No.: PCT/JP98/03483

§ 371 (c)(1),
(2), (4) Date: Dec. 28, 2000

(87) PCT Pub. No.: WO00/00768

PCT Pub. Date: Jan. 6, 2000

(30) Foreign Application Priority Data

Jun. 29, 1998 (JP) .......................................... 10-182858

(51) Int. Cl.⁷ ............................................. A61M 5/175
(52) U.S. Cl. ..................... 604/246; 222/144.5; 222/386; 222/388; 239/305; 239/569; 239/583; 604/246; 604/249
(58) Field of Search ............................... 222/144.5, 386, 222/388; 239/305, 569, 583; 604/246, 249

(56) References Cited

U.S. PATENT DOCUMENTS

| | | | |
|---|---|---|---|
| 4,534,758 A | 8/1985 | Akers et al. | 604/85 |
| 5,232,024 A | 8/1993 | Williams | 137/883 |
| 5,360,407 A | 11/1994 | Leonard | 604/175 |
| 5,391,145 A * | 2/1995 | Dorsey, III | 137/596.2 |
| 5,447,494 A | 9/1995 | Dorsey, III | 604/43 |
| 6,083,205 A * | 7/2000 | Bourne et al. | 137/883 |

FOREIGN PATENT DOCUMENTS

| | | |
|---|---|---|
| EP | 0 135 991 | 4/1995 |
| JP | 57-45836 | 3/1982 |
| JP | 62-149680 | 9/1987 |
| JP | 63-246133 | 10/1988 |
| JP | 06-30905 | 2/1994 |
| JP | 8-308792 | 11/1996 |

* cited by examiner

*Primary Examiner*—Charles G. Freay
*Assistant Examiner*—Emmanuel Sayoc

(57) ABSTRACT

This channel switching apparatus comprises a first channel switching device (303) for switching a first main channel and a second main channel, a second channel switching device (305) for switching a third main channel and a fourth main channel, a third channel switching device (307) for switching a fifth main channel and a sixth main channel, and a fourth channel switching device (308) for switching a seventh main channel and an eighth main channel. Thus, a channel switching apparatus which can readily and correctly perform even by touch can be provided.

3 Claims, 18 Drawing Sheets

[BLOOD ASPIRATING OPERATION]

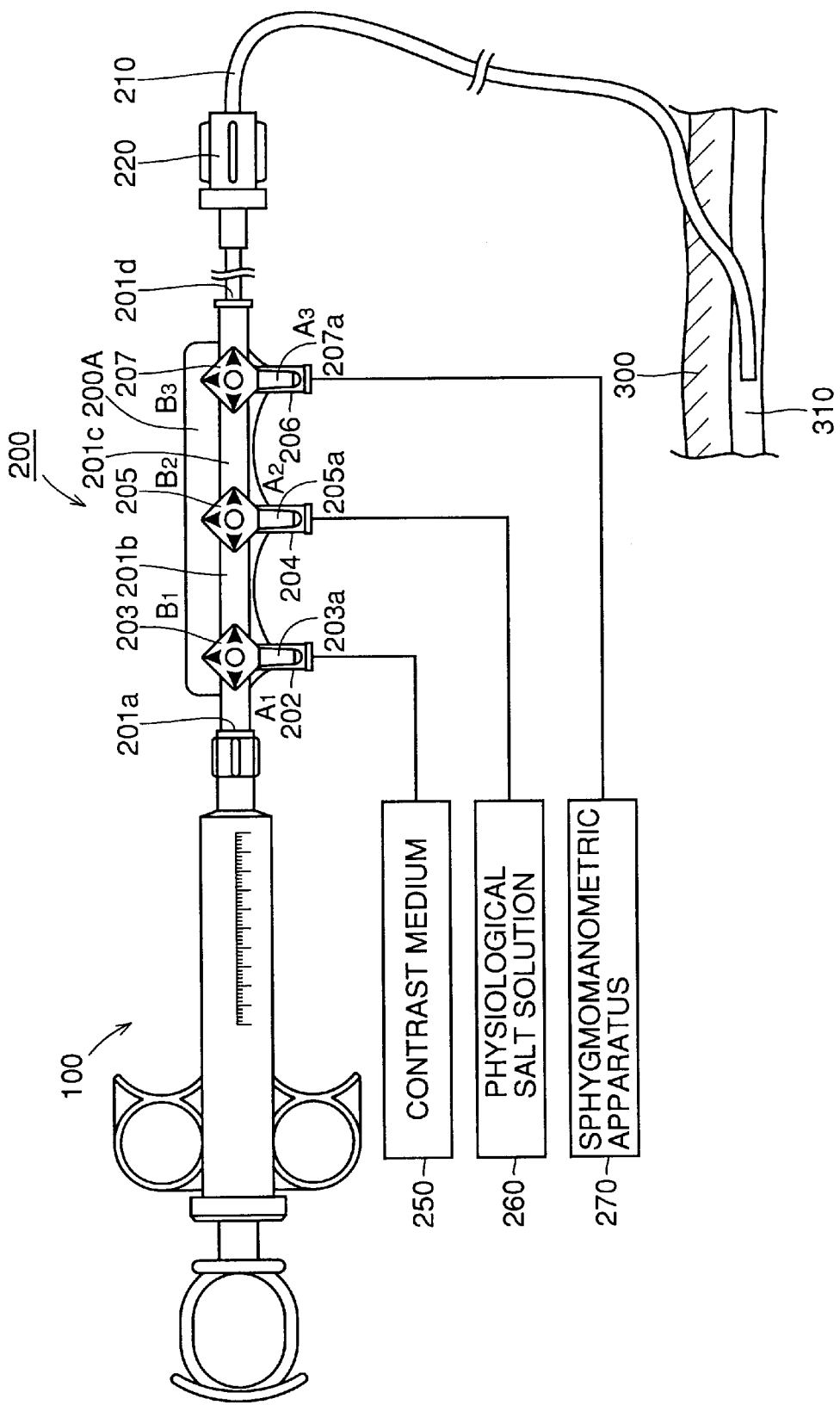

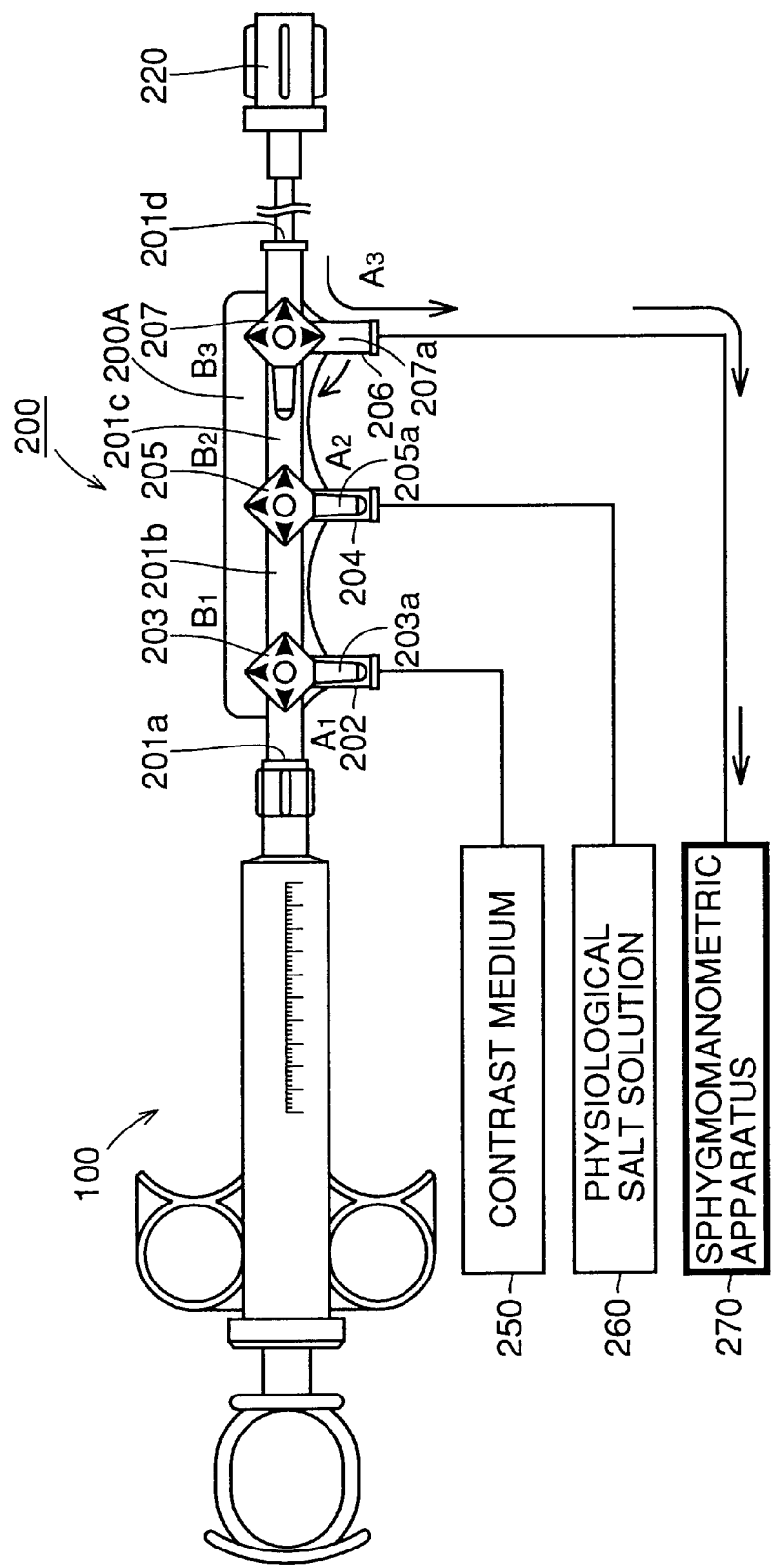
FIG.20 PRIOR ART [SPHYGMOMANOMETRIC OPERATION]

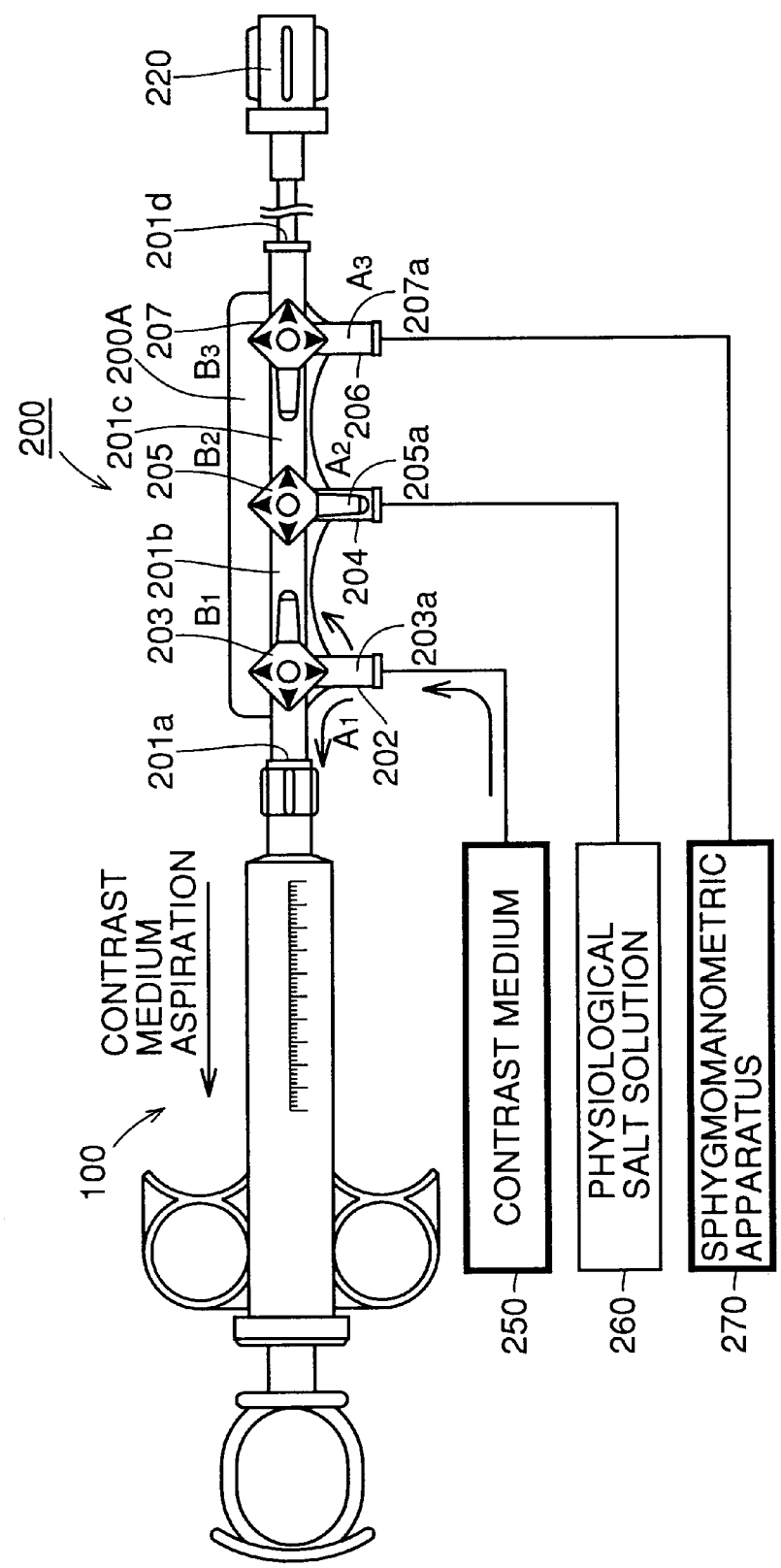
FIG. 21 PRIOR ART [CONTRAST MEDIUM ASPIRATING OPERATION]

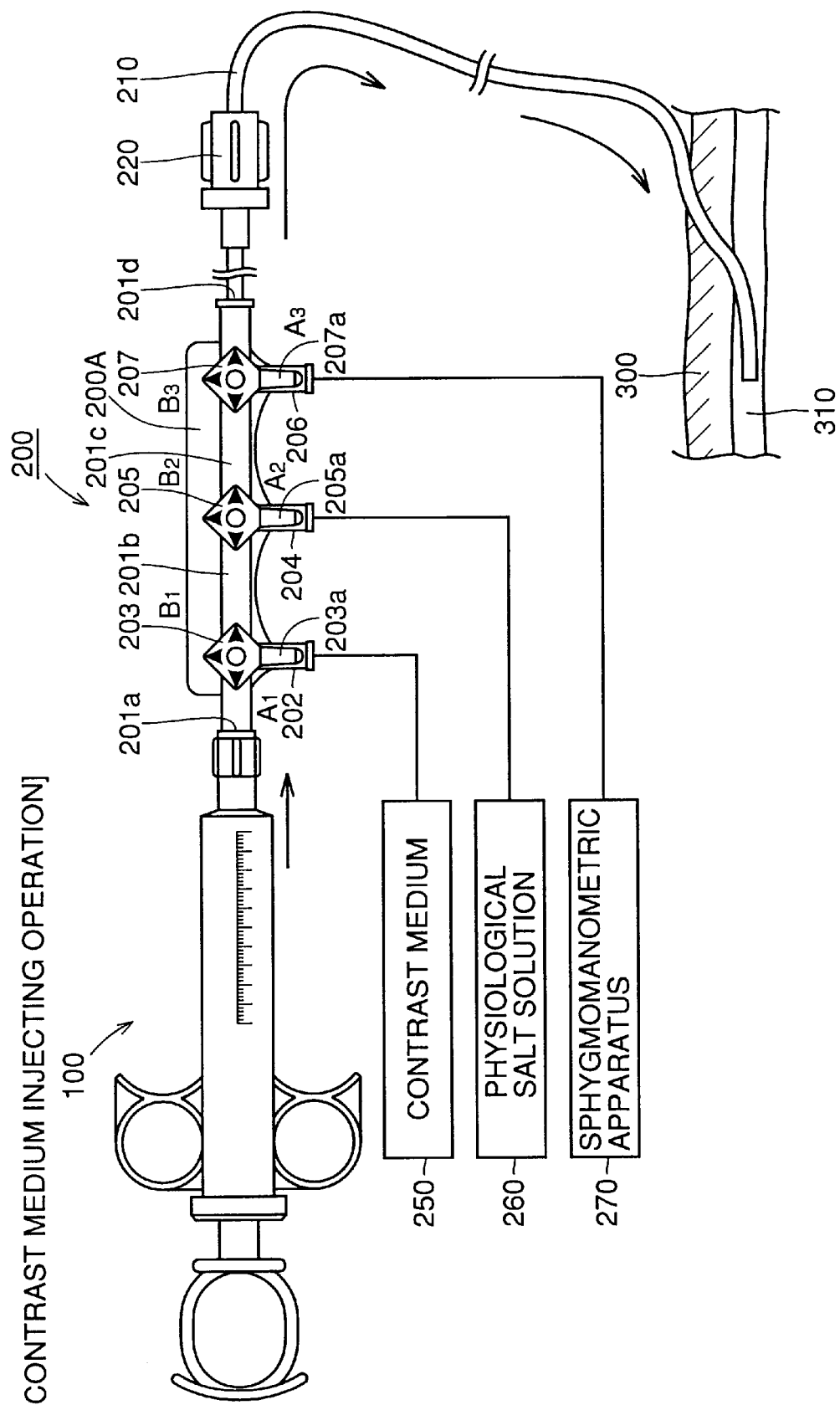

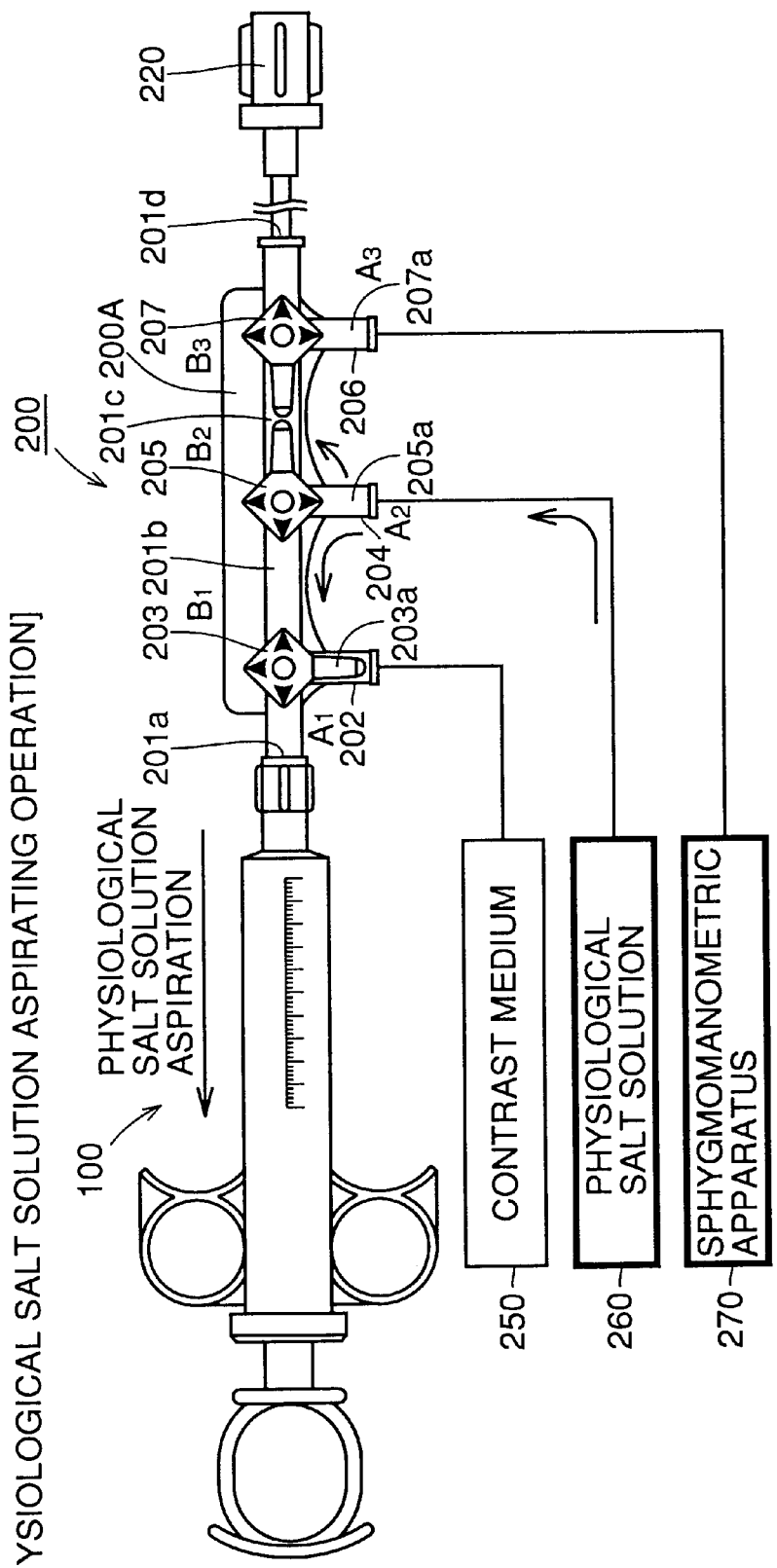

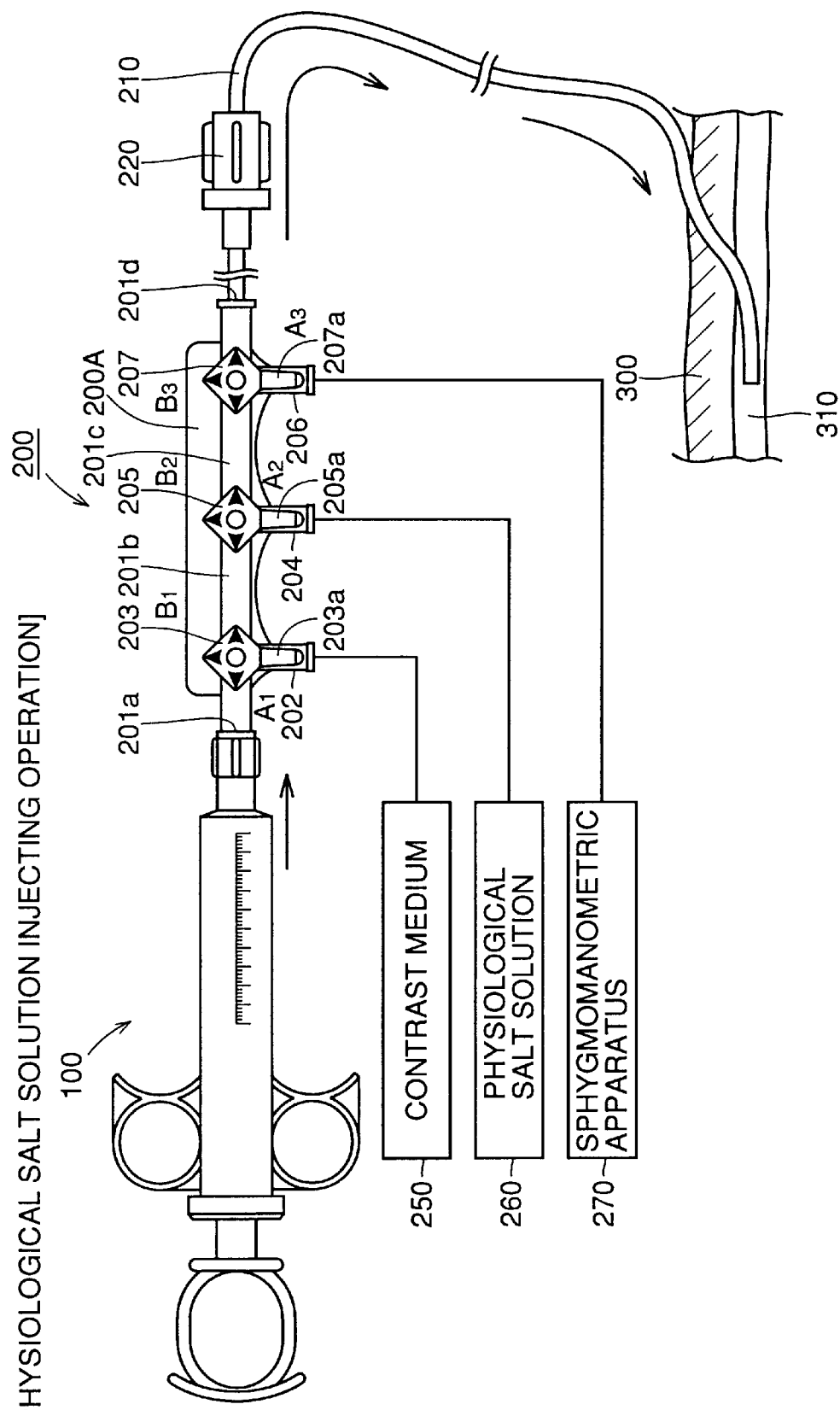

CHANNEL SWITCHING APPARATUS

TECHNICAL FIELD

The present invention relates to a channel switching apparatus, and more specifically, it relates to an improvement of the structure of a channel switching apparatus attaining simplification of manipulation.

BACKGROUND ART

FIG. 19 shows the structure of a manifold 200 employed for an angiographic apparatus employing a contrast medium as an example of a conventional channel switching apparatus.

Referring to the figure, a body part 200A is provided with a first channel 201a, a second channel 201b, a third channel 202, a fourth channel 201c, a fifth channel 204, a sixth channel 201d and a seventh channel 206.

A first cock 203 for switching a first main channel formed by coupling the first channel 201a and the second channel 201b with each other and a second main channel formed by coupling the first channel 201a and the third channel 202 with each other is provided for the first channel 201a, the second channel 201b and the third channel 202.

In the state shown in FIG. 19, the first main channel is formed by the first cock 203 (hereinafter this state is referred to as state A1). The second main channel is formed by rotating a handle 203a of the first cock 203 by 90° anticlockwise (hereinafter this state is referred to as state B1).

A second cock 205 for switching a third main channel formed by coupling the second channel 201b and the fourth channel 201c with each other and a fourth main channel formed by coupling the second channel 201b and the fifth channel 204 with each other is provided for the second channel 201b, the fourth channel 201c and the fifth channel 204. In a state shown in FIG. 20, the third main channel is formed by the second cock 205 (hereinafter this state is referred to as state A2). The fourth main channel is formed by rotating a handle 205a of the second cock 205 by 90° anticlockwise (hereinafter this state is referred to as state B2).

A third cock 207 for switching a fifth main channel formed by coupling the fourth channel 201c and the sixth channel 201d with each other and a sixth main channel formed by coupling the fourth channel 201c and the seventh channel 206 with each other is provided for the fourth channel 201c, the sixth channel 201d and the seventh channel 206.

In the state shown in FIG. 20, the fifth main channel is formed by the third cock 207 (hereinafter this state is referred to as state A3). The sixth main channel is formed by rotating a handle 207a of the third cock 207 by 90° anticlockwise (hereinafter this state is referred to as state B3).

A syringe 100 is connected to one end of the first channel 201a, a contrast medium 250 is connected to the third channel 202 in a flowable manner, a physiological salt solution is connected to the fifth channel 204 in a flowable manner, a sphygmomanometric apparatus 270 is connected to the seventh channel 206, and a catheter 210 having an end introduced into a blood vessel 310 of a case 320 is connected to the sixth channel 201d with interposition of a rotator 220. The rotator 220 is employed for rotating the catheter 210 itself, and the direction of the catheter 210 is so adjusted, that introduction of the contrast medium 250 and the like into the blood vessel 310 is properly performed. A [sphygmomanometric operation], a [contrast medium aspirating operation], a [contrast medium introducing operation], a [physiological salt solution aspirating operation] and a [physiological salt solution introducing operation] are now described with reference to FIG. 20 to FIG. 24.

[Sphygmomanometric Operation]

The sphygmomanometric operation employing the manifold 200 is described with reference to FIG. 20. In the sphygmomanometric operation, the third cock 207 is set in the state B3 for forming the sixth main channel. Thus, blood from the case 320 is introduced into the sphygmomanometric apparatus 270, and the blood pressure of the case 320 is measurable.

[Contrast Medium Aspirating Operation]

The contrast medium aspirating operation employing the manifold 200 is described with reference to FIG. 21. In the contrast medium aspirating operation, the first cock 203 is set in the state B1 for forming the second main channel. Thus, aspiration of the contrast medium 250 employing the syringe 100 is enabled. At this time, the sphygmomanometric operation of the case 320 is continued by maintaining the third cock 207 in the state B3.

[Contrast Medium Introducing Operation]

The contrast medium introducing operation employing the manifold 200 is described with reference to FIG. 22. In the contrast medium introducing operation, the first cock 203 is set in the state A1, the second cock 205 is set in the state A2 and the third cock 207 is set in the state A3, for allowing the first main channel, the third main channel and the fifth main channel to communicate with each other. Thus, it is enabled to introduce the contrast medium 250 stored in the syringe 100 into the blood vessel 310 of the case 320.

[Physiological Salt Solution Aspirating Operation]

The physiological salt solution aspirating operation employing the manifold 200 is described with reference to FIG. 23. In the physiological salt solution aspirating operation, the first cock 203 is set in the state A1 for forming the first main channel while the second cock 205 is set in the state B2 for forming the fourth main channel. Thus, aspiration of a physiological salt solution 260 with the syringe 100 is enabled. At this time, the sphygmomanometric operation of the case 320 is enabled by setting the third cock 207 in the state B3.

[Physiological Salt Solution Introducing Operation]

The physiological salt solution introducing operation employing the manifold 200 is described with reference to FIG. 24. In the physiological salt solution introducing operation, the first cock 203 is set in the state A1, the second cock 205 is set in the state A2 and the third cock 207 is set in the state A3 for allowing the first main channel, the third main channel and the fifth main channel communicate with each other. Thus, it is enabled to introduce the physiological salt solution 260 stored in the syringe 100 into the blood vessel 310 of the case 320. This physiological salt solution 260, which is introduced in order to form no thrombus, is called flush.

A doctor (hereinafter referred to as operator) performing angiography with the manifold 200 having the aforementioned structure must perform each of the aforementioned operations by touch while observing a monitor image of the affected part reflected by X rays. Therefore, the operator must frequently perform switching of each cock with his left hand while holding the syringe 100 with the right hand.

Particularly at the time from the [contrast medium aspirating operation] to the [contrast medium introducing operation] and at the time from the [physiological salt solution aspirating operation] to the [physiological salt solution introducing operation], it is necessary to switch two cocks.

Further, the cocks must necessarily be switched also in each operation, the switching involves troublesomeness while correctness of the switching is required, and there arises such a problem that concentration of the essential important operation for carefully observing the state of the affected part while observing the monitor image cannot be sustained.

Accordingly, an object of the present invention, which has been proposed in order to solve the aforementioned problem, is to provide a channel switching apparatus with which one can readily and correctly perform manipulation of a channel switching apparatus such as a manifold even by touch.

DISCLOSURE OF THE INVENTION

In one aspect of the channel switching apparatus based on the present invention, a channel switching apparatus having a body frame including a first channel, a second channel and a third channel for switching a first main channel formed by coupling the aforementioned first channel and the aforementioned second channel with each other and a second main channel formed by coupling the aforementioned first channel and the aforementioned third channel with each other comprises a switching device provided on an intersection point between the aforementioned first channel, the aforementioned second channel and the aforementioned third channel and having a first coupling channel for coupling the aforementioned first channel and the aforementioned second channel with each other on a first position and a second coupling channel for coupling the aforementioned first channel and the aforementioned third channel with each other on a second position by sliding in a direction substantially perpendicular to a plane including the aforementioned first main channel and the aforementioned second main channel and an urging device for urging the aforementioned switching device so that the aforementioned switching device is urged to be located on the aforementioned first position in a general state and the aforementioned switching device is located on the aforementioned second position only when moved against urging force.

By employing the aforementioned structure, the first main channel is formed in the general state and the second main channel is formed only when moving the aforementioned switching device to the second position against the urging force. When canceling the urging force, therefore, the first main channel of the general state is enabled to return.

Consequently, the first main channel is formed when doing nothing and the switching device may be moved to the second position against the urging force only when needed in order to manipulate this channel switching apparatus, whereby it is enabled to readily and correctly perform manipulation thereof.

In order to execute the aforementioned channel switching apparatus in a more preferable state, the following structure is employed: The aforementioned switching device is a columnar member extending in the direction substantially perpendicular to the plane including the aforementioned first main channel and the aforementioned second main channel, the aforementioned first coupling channel and second coupling channel are provided on its body part with a space in the aforementioned perpendicular direction, a concave part for storing the aforementioned urging device is provided on one end of the aforementioned columnar member, and a recognition area for allowing a person manipulating the channel switching apparatus to tactually recognize the position of the aforementioned switching device is provided on the other end. Preferably, the aforementioned urging device is an elastic member provided between the concave part provided on the aforementioned columnar member and the aforementioned body frame.

By this structure, the manipulating person is enabled to readily and correctly perform the manipulation of the channel switching apparatus even by touch.

In another aspect of the channel switching apparatus based on the present invention, a channel switching apparatus having a first channel, a second channel and a third channel for switching a first main channel formed by coupling the aforementioned first channel and the aforementioned second channel with each other and a second main channel formed by coupling the aforementioned first channel and the aforementioned third channel comprises a switching device provided on an intersection point between the aforementioned first channel, the aforementioned second channel and the aforementioned third channel for sliding between a first position and a second position in a plane including the aforementioned first main channel and the aforementioned second main channel thereby coupling the aforementioned first channel and the aforementioned second channel with each other on the first position and coupling the aforementioned first channel and the aforementioned third channel with each other on the aforementioned second position, and an urging device for urging the aforementioned switching device so that the aforementioned switching device is urged to be located on the aforementioned first position in a general state and the aforementioned switching device is located on the aforementioned second position against urging force only when the flow rate in the aforementioned third channel exceeds a prescribed value.

By employing the aforementioned structure, the first main channel is formed in the general state while the aforementioned switching device is located on the aforementioned second position against the urging force and the second main channel is formed only when the flow rate in the aforementioned third channel exceeds the prescribed value. When the flow rate in the aforementioned third channel lowers below the prescribed value, the first main channel is enabled to return.

Consequently, a person manipulating this channel switching apparatus is enabled to switch the first main channel and the second main channel only by adjustment of the flow rate in the third channel, and enabled to readily and correctly perform manipulation of the channel switching apparatus.

In order to execute the aforementioned channel switching apparatus in a more preferable state, the following structure is employed: The aforementioned switching device is a valve element, and the urging device is an elastic member arranged to shut off the aforementioned third channel with the aforementioned valve element in the general state.

In still another aspect of the channel switching apparatus based on the present invention, it comprises a body frame including a first channel, a second channel, a third channel, a fourth channel, a fifth channel, a sixth channel, a seventh channel, and an eighth channel and a ninth channel diverging from the aforementioned fourth channel, a first channel switching device for switching a first main channel formed by coupling the aforementioned first channel and the aforementioned second channel with each other and a second main channel formed by coupling the aforementioned first channel and the aforementioned third channel with each other, a second channel switching device for switching a third main channel formed by coupling the aforementioned second channel and the aforementioned fourth channel with each other and a fourth main channel formed by coupling the aforementioned second channel and the aforementioned fifth channel with each other, a third channel switching device for switching a fifth main channel formed by coupling the aforementioned fourth channel and the aforementioned sixth channel with each other and a sixth main channel formed by coupling the aforementioned sixth channel and the aforementioned ninth channel with each other, and a fourth channel switching device for switching a seventh main channel formed by coupling the aforementioned seventh channel and the aforementioned ninth channel with each other and an eighth main channel formed by coupling the aforementioned eighth channel and the aforementioned ninth channel with each other.

Further, the aforementioned first channel switching device has a first switching device provided on an intersection point between the aforementioned first channel, the aforementioned second channel and the aforementioned third channel and having a first coupling channel for coupling the aforementioned first channel and the aforementioned second channel with each other on a first position and a second coupling channel for coupling the aforementioned first channel and the aforementioned third channel with each other on a second position by sliding in a direction substantially perpendicular to a plane including the aforementioned first main channel and the aforementioned second main channel and a first urging device for urging the aforementioned first switching device so that the aforementioned first switching device is urged to be located on the aforementioned first position in a general state and the aforementioned first switching device is located on the aforementioned second position only when moved against urging force, the aforementioned second channel switching device has a second switching device provided on an intersection point between the aforementioned second channel, the aforementioned fourth channel and the aforementioned fifth channel and having a third coupling channel for coupling the aforementioned second channel and the aforementioned fourth channel with each other on a first position and a fourth coupling channel for coupling the aforementioned second channel and the aforementioned fifth channel with each other on a second position by sliding in a direction substantially perpendicular to a plane including the aforementioned third main channel and the aforementioned fourth main channel and a second urging device for urging the aforementioned second switching device so that the aforementioned second switching device is urged to be located on the aforementioned first position in a general state and the aforementioned second switching device is located on the aforementioned second position only when moved against urging force, the aforementioned third channel switching device has a third switching device provided on an intersection point between the aforementioned fourth channel, the aforementioned sixth channel and the aforementioned ninth channel and having a fifth coupling channel for coupling the aforementioned sixth channel and the aforementioned ninth channel with each other on a first position and a sixth coupling channel for coupling the aforementioned sixth channel and the aforementioned fourth channel with each other on a second position by sliding in a direction substantially perpendicular to a plane including the aforementioned fifth main channel and the aforementioned sixth main channel and a third urging device for urging the aforementioned third switching device so that the aforementioned third switching device is urged to be located on the aforementioned first position in a general state and the aforementioned third switching device is located on the aforementioned second position only when moved against urging force, and the aforementioned fourth channel switching device has a fourth switching device provided on an intersection point between the aforementioned seventh channel, the aforementioned eighth channel and the aforementioned ninth channel for moving between a first position and a second position in a plane including the aforementioned seventh main channel and the aforementioned eighth main channel thereby coupling the aforementioned seventh channel and the aforementioned ninth channel with each other on the aforementioned first position and coupling the aforementioned ninth channel and the aforementioned eighth channel with each other on the aforementioned second position and a fourth urging device for urging the aforementioned fourth switching device so that the aforementioned fourth switching device is urged to be located on the aforementioned first position in a general state and the aforementioned fourth switching device is located on the aforementioned second position against urging force only when the flow rate in the aforementioned eighth channel exceeds a prescribed value.

By employing the aforementioned structure, the first channel, the third channel and the fourth channel communicate with each other in the general state, and it is further enabled to implement such a state that the sixth channel, the ninth channel and the seventh channel communicate with each other.

Further, the first channel and the second channel are shut off and the second main channel is formed only when moving the first switching device to the second position against the urging force. When canceling the urging force, therefore, the general state of such a state that the first main channel and the third main channel communicate with each other is enabled to return.

The second channel and the fourth channel are shut off and the fourth main channel is formed only when moving the second switching device to the second position against the urging force. When canceling the urging force, therefore, the general state of such a state that the first main channel and the third main channel communicate with each other is enabled to return.

The sixth channel and the ninth channel are shut off and the fifth main channel is formed only when moving the third switching device to the second position against the urging force. When canceling the urging force, therefore, the general state of such a state that the sixth channel and the ninth channel communicate with each other is enabled to return.

The aforementioned fourth switching device is located on the aforementioned second position against the urging force and the eighth main channel is formed only when the flow rate in the eighth channel exceeds the prescribed value. When the flow rate in the aforementioned eighth channel lowers below the prescribed value, the seventh main channel is enabled to return.

Consequently, the first main channel is formed when doing nothing and the switching device may be moved to the second position against the urging force only when needed, in order to manipulate this passage switching apparatus. Further, switching between the seventh main channel and the eighth main channel is enabled only by adjustment of the flow rate in the eighth channel. Consequently, it is enabled to readily and correctly perform manipulation thereof.

In order to execute the aforementioned channel switching apparatus in a more preferable state, the following structure is employed: The aforementioned first switching device is a first columnar member extending in the direction substantially perpendicular to the plane including the aforementioned first main channel and the aforementioned second main channel, the aforementioned first coupling channel and the aforementioned second coupling channel are provided on its body part with a space in the aforementioned perpendicular direction, a first concave part for storing the aforementioned urging device is provided on an end of the aforementioned columnar member while a first recognition area for allowing a person manipulating the channel switching apparatus to tactually recognize the position of the aforementioned first switching device is provided on the other end, the aforementioned second switching device is a second columnar member extending in the direction substantially perpendicular to the plane including the aforementioned third main channel and the aforementioned fourth main channel, the aforementioned third coupling channel and the aforementioned fourth coupling channel are provided on its body part with a space in the aforementioned perpendicular direction, a second concave part for storing the aforementioned urging device is provided on an end of the aforementioned second columnar member while a second recognition area for allowing the person manipulating the channel switching apparatus to tactually recognize the position of the aforementioned second switching device is provided on the other end, the aforementioned third switching device is a third columnar member extending in the direction substantially perpendicular to the plane including the aforementioned fifth main channel and the aforementioned sixth main channel, the aforementioned fifth coupling channel and the aforementioned sixth coupling channel are provided on its body part with a space in the aforementioned perpendicular direction, a third concave part for storing the aforementioned urging device is provided on an end of the aforementioned third columnar member while a third recognition area for allowing the person manipulating the channel switching apparatus to tactually recognize the position of the aforementioned third switching device is provided on the other end, and different shapes are provided for the aforementioned first recognition area, second recognition area and third recognition area respectively.

By this structure, the manipulating person is enabled to readily and correctly perform manipulation of the first channel switching device, the second channel switching device and the third channel switching device even by touch.

Preferably, a syringe having a piston is connected to the aforementioned first channel, a contrast medium is connected to the aforementioned third channel in a flowable manner, a physiological salt solution is connected to the aforementioned fifth channel in a flowable manner, another end of a catheter having an end introduced into a blood vessel of a human body is connected to the aforementioned sixth channel, and a sphygmomanometric apparatus is connected to the aforementioned seventh channel.

In a further aspect of the channel switching apparatus based on the present invention, a channel switching apparatus having a body frame including a first channel, a second channel and a third channel for switching a first main channel formed by coupling the aforementioned first channel and the aforementioned second channel with each other and a second main channel formed by coupling the aforementioned first channel and the aforementioned third channel with each other comprises a switching device provided on an intersection point between the aforementioned first channel, the aforementioned second channel and the aforementioned third channel and having a coupling channel for coupling the aforementioned first channel and the aforementioned second channel with each other on a first position and coupling the aforementioned first channel and the aforementioned third channel with each other on a second position by sliding in a direction substantially perpendicular to a plane including the aforementioned first main channel and the aforementioned second main channel and an urging device for urging the aforementioned switching device so that the aforementioned switching device is urged to be located on the aforementioned first position in a general state and the aforementioned switching device is located on the aforementioned second position only when moved against urging force.

By employing the aforementioned structure, the first main channel is formed in the general state and the second main channel is formed only when moving the aforementioned switching device to the second position against the urging force. When canceling the urging force, therefore, the first main channel of the general state is enabled to return.

Consequently, the first main channel is formed when doing nothing while the switching device may be moved to the second position against the urging force only when needed in order to manipulate this channel switching apparatus, whereby it is enabled to readily and correctly perform manipulation thereof.

BRIEF DESCRIPTION OF THE DRAWINGS

FIG. 3 is a perspective view showing the structure of a first switching button 303a.

FIG. 4 is a perspective view showing the structure of a second switching button 305a.

FIG. 5 is a perspective view showing the structure of a third switching button 307a.

FIG. 14 is a perspective view showing another structure of the first switching button 303a.

FIG. 15 is a perspective view showing still another structure of the first switching button 303a.

FIG. 19 is a plan view showing the structure of a manifold 200 in the prior art.

FIG. 20 is a model diagram showing a [sphygmomanometric operation] employing the manifold 200 in the prior art.

FIG. 21 is a model diagram showing a [contrast medium aspirating operation] employing the manifold 200 in the prior art.

FIG. 22 is a model diagram showing a [contrast medium introducing operation] employing the manifold 200 in the prior art.

FIG. 23 is a model diagram showing a [physiological salt solution aspirating operation] employing the manifold 200 in the prior art.

FIG. 24 is a model diagram showing a [physiological salt solution introducing operation] employing the manifold 200 in the prior art.

BEST MODES FOR CARRYING OUT THE INVENTION

Channel switching apparatuses in embodiments based on the present invention are now described with reference to the drawings. As an example of the channel switching apparatus, a case of applying the same to a manifold employed for an angiographic apparatus employing a contrast medium similarly to the prior art is described.

(Embodiment 1)

Figure 1:
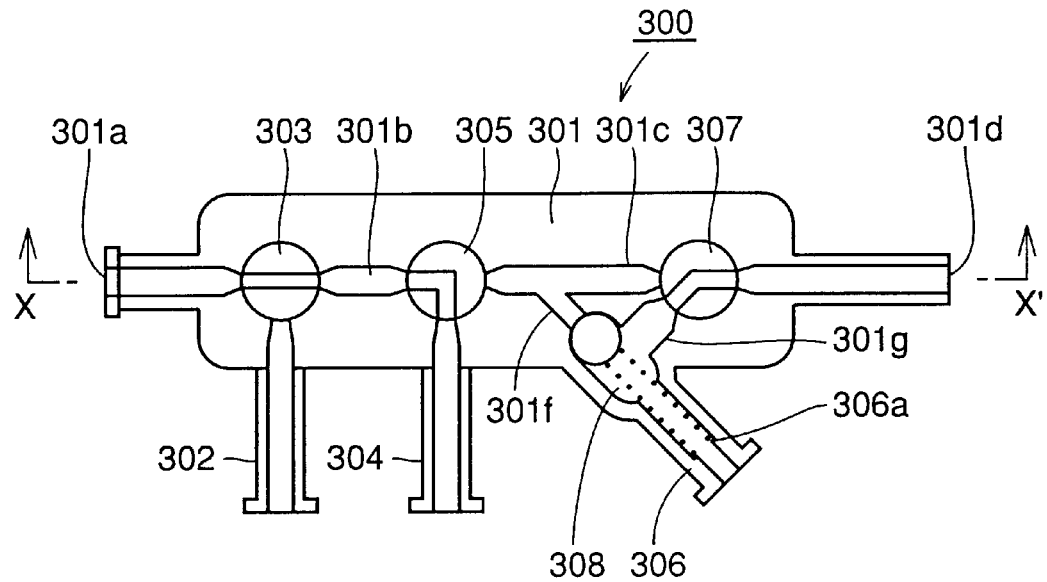
FIG. 1 is a plan view showing the structure of a manifold 300 in an embodiment 1.
Figure 2:
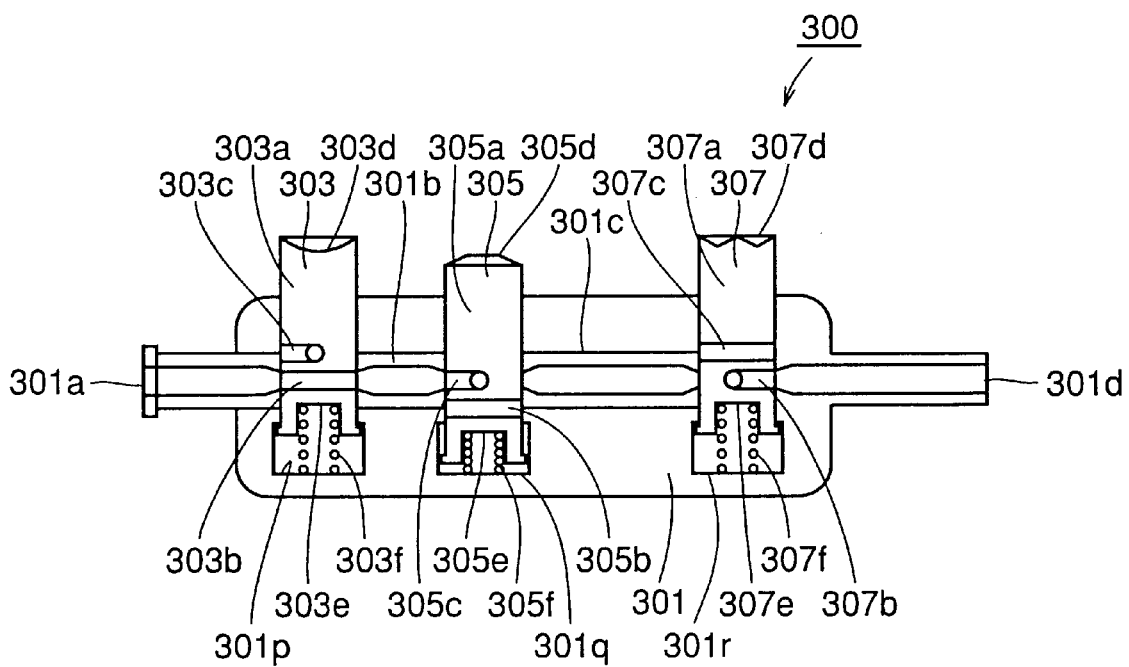
FIG. 2 is a sectional view taken along the line X–X' in FIG. 1.

FIG. 1 and FIG. 2 show the structure of a manifold 300 in this embodiment. FIG. 1 shows a plan view of the manifold 300, and FIG. 2 is a sectional view taken along the line X–X' in FIG. 1.

Referring to both figures, a body part 301 is provided with a first channel 301a, a second channel 301b, a third channel 302, a fourth channel 301c, a fifth channel 304, a sixth channel 301d, a seventh channel 306, and an eighth channel 301f and a ninth channel 301g diverging from the fourth channel 301c.

A first main channel is formed by coupling the first channel 301a and the second channel 301b with each other. A second main channel is formed by coupling the first channel 301a and the third channel 302 with each other. A first channel switching device 303 for switching the first main channel and the second main channel is provided on an intersection point between the first channel 301a, the second channel 301b and the third channel 302.

A third main channel is formed by coupling the second channel 301b and the fourth channel 301c with each other. A fourth main channel is formed by coupling the second channel 301b and the fifth channel 304 with each other. A second channel switching device 305 provided on an intersection point between the second channel 301b, the fourth channel 301c and the fifth channel 304 for switching the third main channel and the fourth main channel is provided.

A fifth main channel is formed by coupling the fourth channel 301c and the sixth channel 301d with each other. A sixth main channel is formed by coupling the sixth channel 301d and the ninth channel 301g with each other. A third channel switching device 307 provided on an intersection point between the sixth channel 301d and the ninth channel 301g for switching the fifth main channel and the sixth main channel is provided.

A seventh main channel is formed by coupling the seventh channel 306 and the ninth channel 301g with each other. An eighth main channel is formed by coupling the eighth channel 301f and the ninth channel 301g with each other. A fourth channel switching device 308 provided on an intersection point between the seventh channel 306, the eighth channel 301f and the ninth channel 301g for switching the seventh main channel and the eighth main channel is provided.

Figure 3:
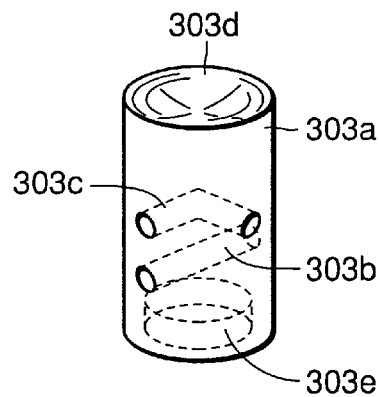

Referring to FIG. 2 and FIG. 3, the first channel switching device 303 has a columnar first switching button 303a having a first coupling channel 303b for coupling the first channel 301a and the second channel 301b with each other on a first position and a second coupling channel 303c for coupling the first channel 301a and the third channel 302 with each other on a second position by sliding in a direction substantially perpendicular to a plane including the first main channel and the second main channel, and a first coil spring 303f for urging the first switching button 303a so that the first switching button 303a is urged to be located on the first position in a general state and the first switching button 303a is located on the second position only when moved against urging force.

This first coil spring 303f is arranged between a first concave part 303e provided on the first switching button 303a and a first concave part 301p provided on the body frame 301.

The first switching button 303a is provided with a first recognition concave part 303d for allowing a person manipulating the manifold 300 to tactually recognize the position of the first switching button 303a.

Such a state that the first switching button 303a is on the first position is referred to as state A1, and such a state that the first switching button 303a is on the second position is referred to as state A2.

Figure 4:
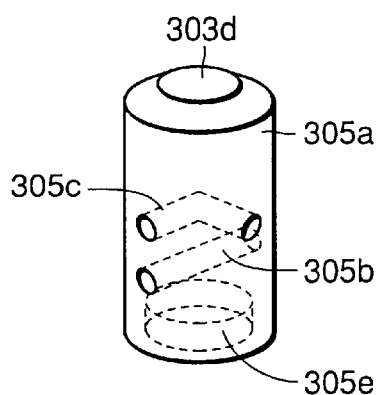

Referring to FIG. 2 and FIG. 4, the second channel switching device 305 has a second switching button 305a having a third coupling channel 305b for coupling the second channel 301b and the fourth channel 301c with each other on a first position by sliding in a direction substantially perpendicular to a plane including the third main channel and the fourth main channel and a fourth coupling channel 305c for coupling the second channel 301b and the fifth channel 304 with each other on a second position and a second coil spring 305f for urging the second switching button 305a so that the second switching button 305a is urged to be located on the first position in a general state and the second switching button 305a is located on the second position only when moved against urging force.

This second coil spring 305f is arranged between a second concave part 305e provided on the second switching button 305a and a second concave part 301q provided on the body frame 301.

The second switching button 305a is provided with a second recognition convex part 305d for allowing the person manipulating the manifold 300 to tactually recognize the position of the second switching button 305a.

Such a state that the second switching button 305a is on the first position is referred to as state B1, and such a state that the second switching button 305a is on the second position is referred to as state B2.

Figure 5:
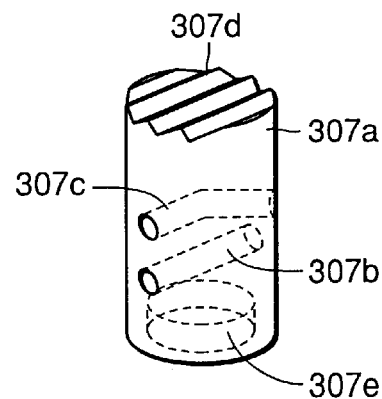

Referring to FIG. 2 and FIG. 5, the third channel switching device 307 has a third switching button 307a having a fifth coupling channel 307b for coupling the sixth channel 301d and the ninth channel 301g with each other on a first position by sliding in a direction substantially perpendicular to a plane including the fourth channel 301c, the fifth main channel and the sixth main channel and a sixth coupling channel 307c for coupling the sixth channel 301d and the fourth channel 301c with each other on a second position and a third coil spring 307f for urging the third switching button 307a so that the third switching button 307a is urged to be located on the first position in a general state and the third switching button 307a is located on the second position only when moved against urging force.

This third coil spring 307f is arranged between a first concave part 307e provided on the third switching button 307a and a third concave part 301r provided on the body frame 301.

The third switching button 307a is provided with a third recognition concave/convex part 307d for allowing the person manipulating the manifold 300 to tactually recognize the position of the third switching button 307a.

Such a state that the third switching button 307a is on the first position is referred to as state C1, and such a state that the third switching button 307a is on the second position is referred to as state C2.

Figure 6:
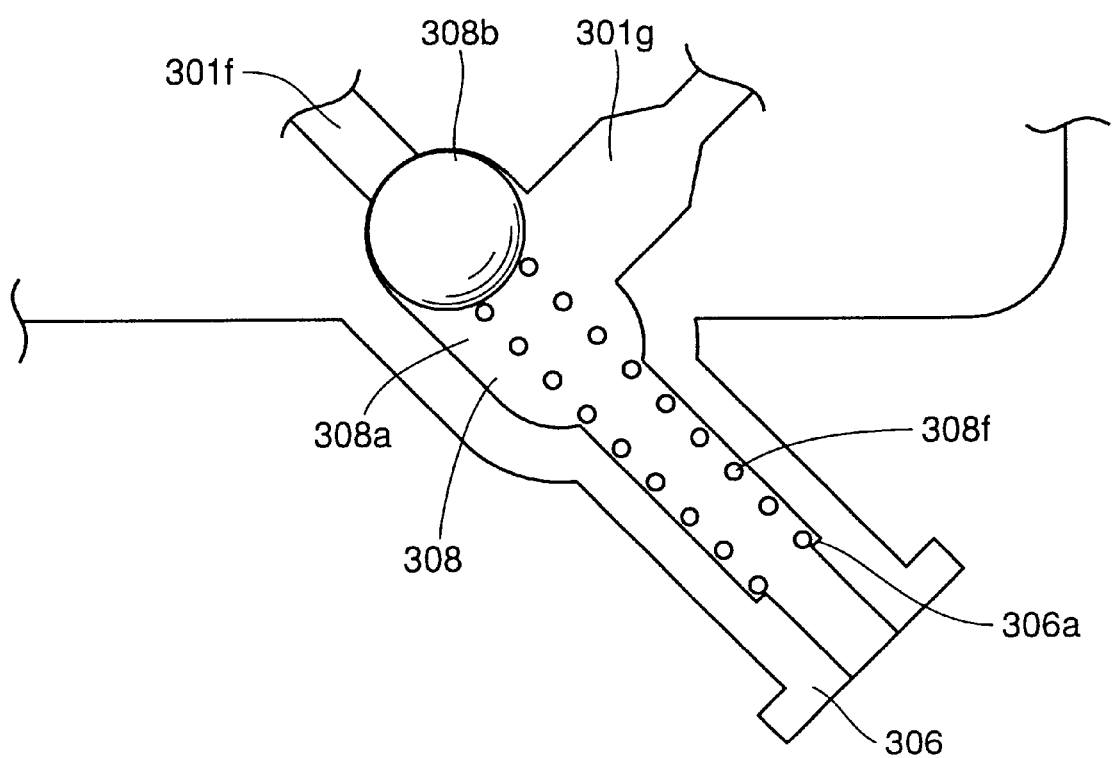
FIG. 6 is a plan view showing the structure of a fourth channel switching device 308.

Referring to FIG. 1 and FIG. 6, the fourth channel switching device 308 has a ball valve 308b for moving between a first position and a second position in a plane including the seventh main channel and the eighth main channel thereby coupling the seventh channel 306 and the ninth channel 301g with each other on the first position and coupling the ninth channel 301g and the eighth channel 301f with each other on the second position, a ball valve chest 308a instructing movement of this ball valve 308b and a fourth coil spring 308f for urging the ball valve 308b so that the ball valve 308b is urged to be located on the first position in a general state and the ball valve 308b is located on the second position against urging force only when the flow rate in the eighth channel 30 if exceeds a prescribed value.

This fourth coil spring 307f is provided between a step part 306a provided on the seventh channel 306 and the ball valve 308b.

Such a state that the ball valve 308b is on the first position is referred to as state D1, and such a state that the ball valve 308b is on the second position is referred to as state D2.

While members of columnar shapes are employed as the shapes of the aforementioned first switching button 303a, second switching button 305a and third switching button 307a, the present invention is not necessarily restricted to this shape but any shape is employable so far as the same has a similar function. Further, the first coil spring 303f, the second coil spring 305f and the third coil spring 307f are not restricted to the coil springs either but elastic members of any shapes are employable so far as the same have similar functions.

A [sphygmomanometric operation], a [contrast medium aspirating operation], a [contrast medium introducing operation], a [physiological salt solution aspirating operation] and a [physiological salt solution introducing operation] employing the manifold 300 having the aforementioned structure are now described with reference to FIG. 7 to FIG. 12. As shown in each figure, it is assumed that a syringe 100 is connected to one end of the first channel 301a of the manifold 300, a contrast medium 250 is connected to the third channel 302 in a flowable manner, a physiological salt solution is connected to the fifth channel 304 in a flowable manner, a sphygmomanometlic apparatus 270 is connected to the seventh channel 306, and a catheter 210 having an end introduced into a blood vessel of a case similarly to the case of the prior art is connected to the sixth channel 301d with interposition of a rotator 220.

[Sphygmomanometric Operation]

Figure 7:
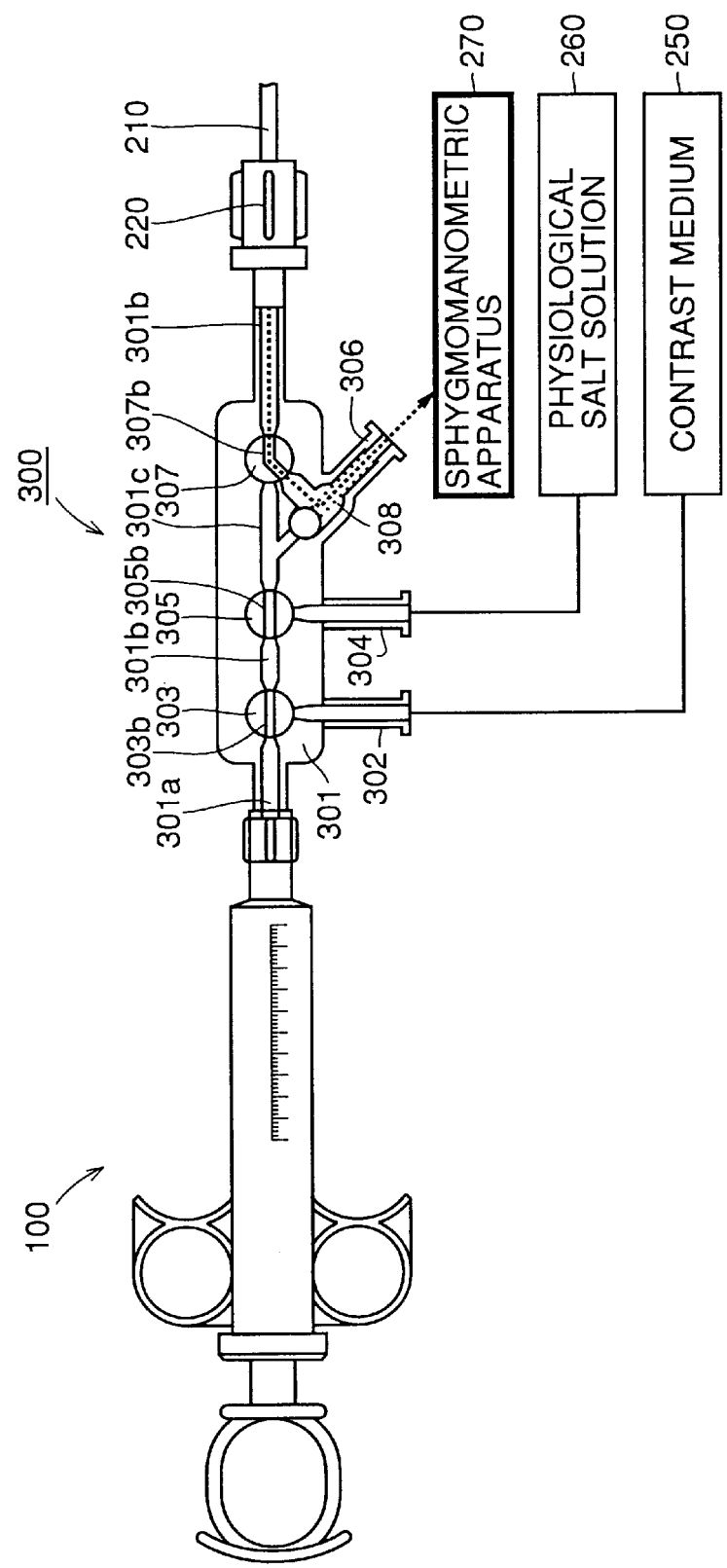
FIG. 7 is a model diagram showing a [sphygmomanometric operation] employing the manifold 300 in the embodiment 1.

With reference to FIG. 7, the sphygmomanometric operation employing the manifold 300 is described. In the sphygmomanometric operation, an operator may manipulate nothing but the sixth main channel and the seventh main channel enter open states due to the third channel switching device 307 being in the state C1 and the fourth channel switching device 308 being in the state D1, the blood from the case is introduced into the sphygmomanometlic apparatus 270, and the blood pressure of a case 320 is measurable.

[Contrast Medium Aspirating Operation]

Figure 8:
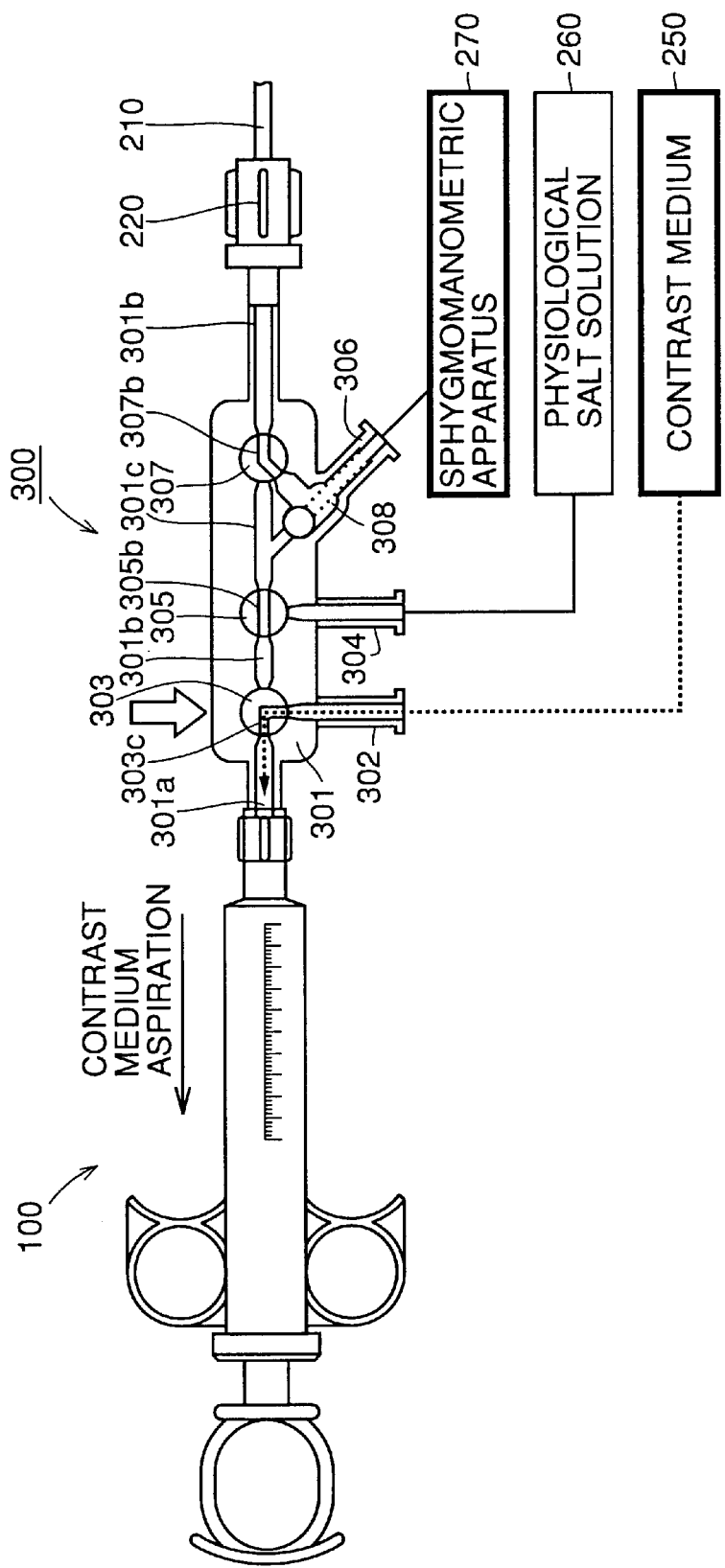
FIG. 8 is a model diagram showing a [contrast medium aspirating operation] employing the manifold 300 in the embodiment 1.

With reference to FIG. 8, the contrast medium aspirating operation employing the manifold 300 is described. In the contrast medium aspirating operation, the state A2 is attained while pressing the first switching button 303a of the first channel switching device 303, for forming the second main channel. Thus, aspiration of the contrast medium 250 employing the syringe 100 is enabled. At this time, sphygmomanometry of the case 320 is continued as such in the third channel switching device 307.

[Contrast Medium Introducing Operation]

Figure 9:
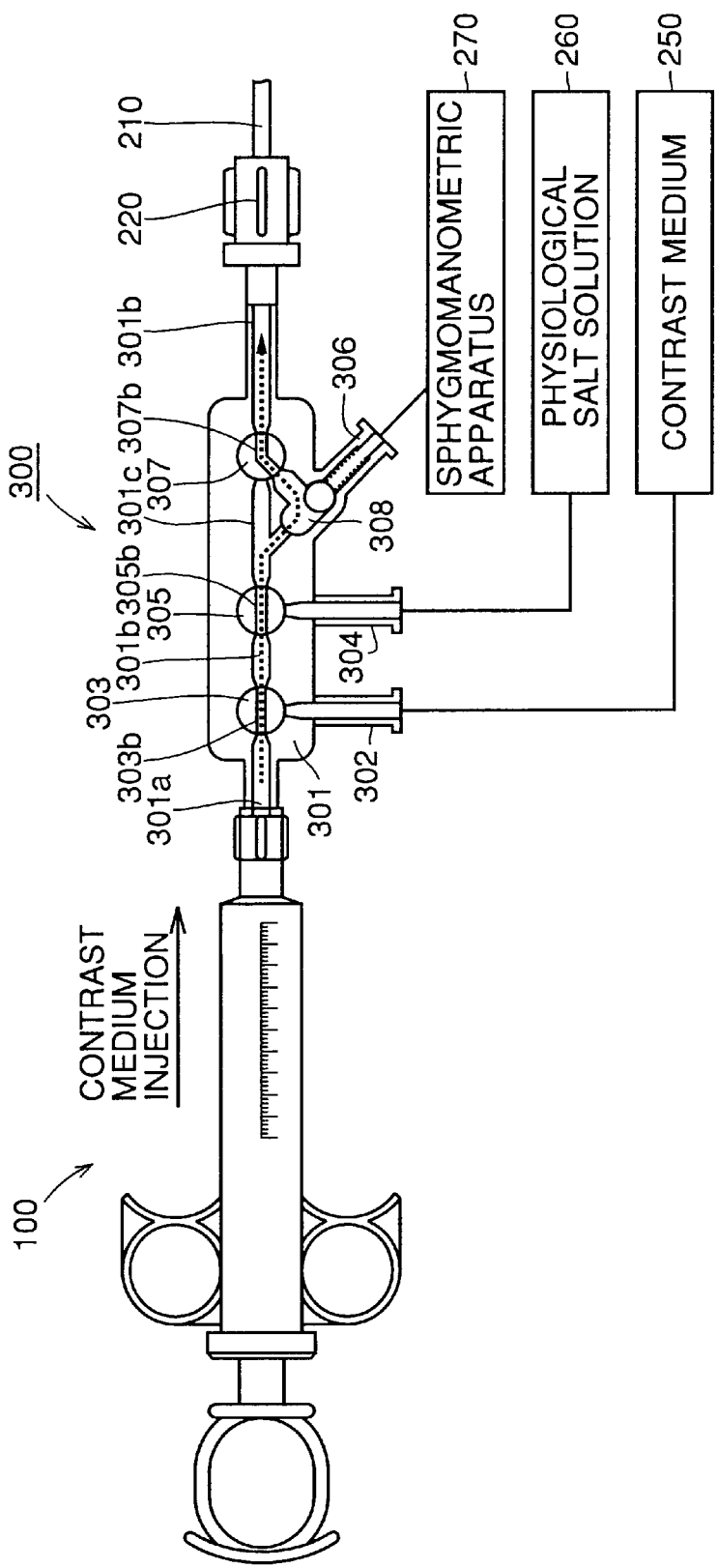
FIG. 9 is a model diagram showing a [contrast medium introducing operation] employing the manifold 300 in the embodiment 1.

With reference to FIG. 9, the contrast medium introducing operation employing the manifold 300 is described. In the contrast medium introducing operation, pressing of the first switching button 303a of the aforementioned first channel switching device 303 is canceled to attain the state A1, for starting introduction of the contrast medium 250 employing the syringe 100. At this time, a flow rate exceeding a prescribed value takes place in the eighth channel 308f in the fourth channel switching device 308, and hence the ball valve 308b moves to the second position against the urging force, the fourth channel switching device 308 enters the state D2, and the eighth main channel enters an open state. Consequently, it is enabled to introduce the contrast medium stored in the syringe 100 into the case.

At this time, the third channel switching device 307 automatically returns to the state D1 due to change of pressure in the seventh main channel and the eighth main channel, and sphygmomanometry of the case 320 is restarted.

Figure 10:
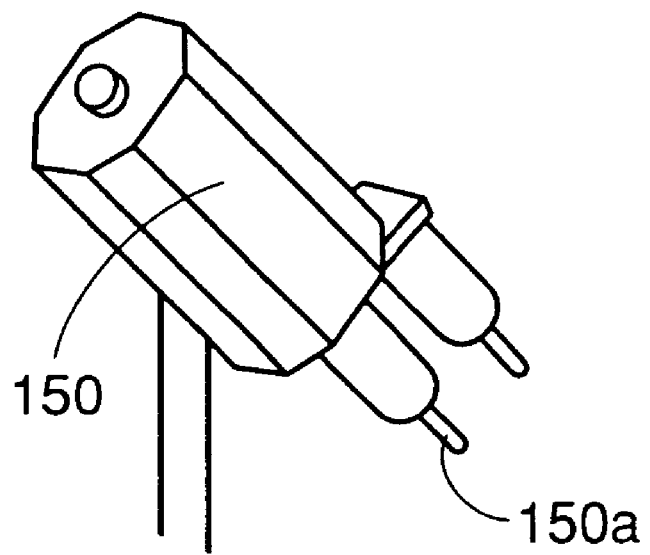
FIG. 10 is a perspective view showing a schematic structure of a contrast medium introduction device 150.

The present invention is not restricted to the case of employing the syringe 100 in the contrast medium introducing operation but it is also possible to employ a contrast medium introducing apparatus 150 shown in FIG. 10, for example, for coupling an outlet 150a of the contrast medium introducing apparatus 150 and the first channel 301a with each other.

[Physiological Salt Solution Aspirating Operation]

Figure 11:
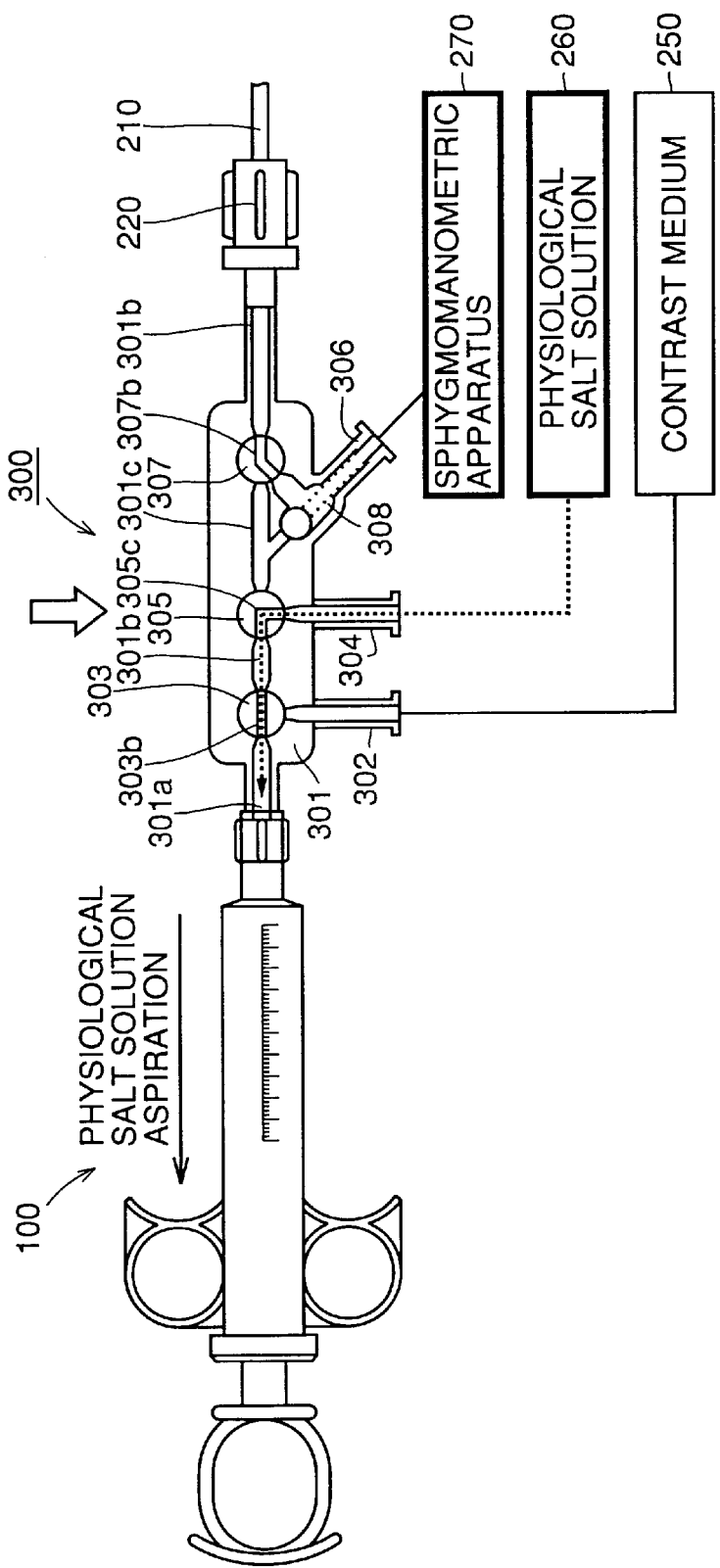
FIG. 11 is a model diagram showing a [physiological salt solution aspirating operation] employing the manifold 300 in the embodiment 1.

With reference to FIG. 11, the physiological salt solution aspirating operation employing the manifold 300 is described. In the physiological salt solution aspirating operation, the state B2 is attained while pressing the second switching button 305a of the second channel switching device 305, for forming the fourth main channel. Thus, the first main channel and the fourth main channel communicate with each other, and aspiration of a physiological salt solution 260 employing the syringe 100 is enabled.

[Physiological Salt Solution Introducing Operation]

Figure 12:
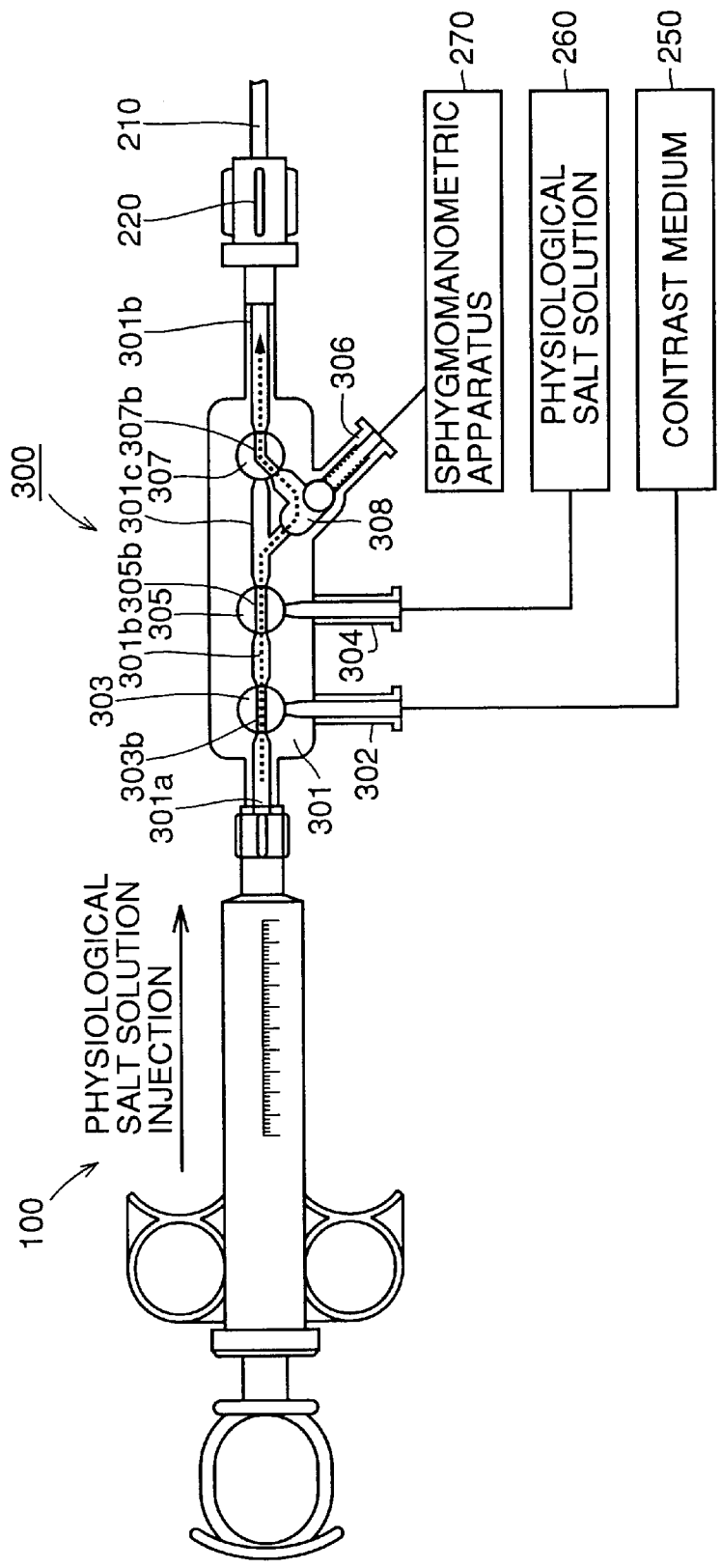
FIG. 12 is a model diagram showing a [physiological salt solution introducing operation] employing the manifold 300 in the embodiment 1.

With reference to FIG. 12, the physiological salt solution introducing operation employing the manifold 300 is described. In the physiological salt solution introducing operation, the pressing of the first switching button 305a of the aforementioned second channel switching device 305 is canceled to attain the state B1, for starting introduction of the physiological salt solution 260 employing the syringe 100.

At this time, the pressure in the eighth channel 308f rises in the fourth channel switching device 308, and hence the ball valve 308b moves to the second position against the urging force, the fourth channel switching device 308 enters the state D2, and the eighth main channel enters an open state. Consequently, it is enabled to introduce the physiological salt solution stored in the syringe 100 into the case 320.

Figure 13:
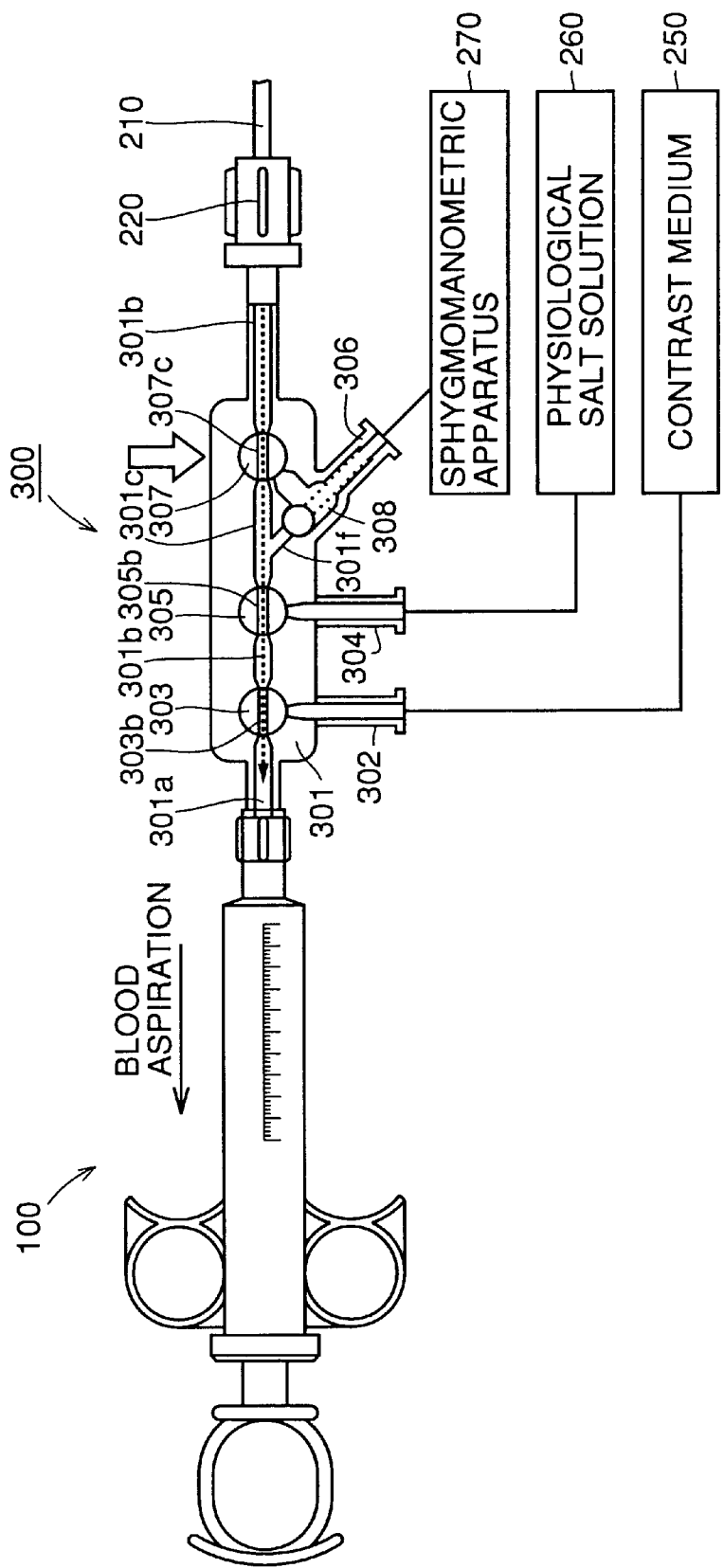
FIG. 13 is a model diagram showing a [blood aspirating operation] employing the manifold 300 in the embodiment 1.

In the manifold 300 in this embodiment, the first main channel, the second main channel and the fifth main channel enter communicating states by attaining the state C2 while pressing the third switching button 307a of the third channel switching device 307 as shown in FIG. 13, and hence it is also enabled to readily perform aspiration of the blood of the case with inside the syringe 100.

According to the manifold 300 in this embodiment, as hereinabove described, it is enabled to perform each operation only by pushing either switching button of the first switching button 303a of the first channel switching device 303, the second switching button 305a of the second channel switching device 305 or the third switching button 307a of the third channel switching device 307, and it is enabled to reduce the quantity of manipulation required to the operator.

Further, the first switching button 303a, the second switching button 305a and the third switching button 307a are provided with the first recognition concave part 303d, the second recognition convex part 305d and the third recognition concave/convex part 307d for recognizing the positions respectively, whereby it is enabled to reliably perform manipulation of the respective first channel switching device 303, second channel switching device 305 and third channel switching device 307 also in operations of the operator by touch.

Figure 14:
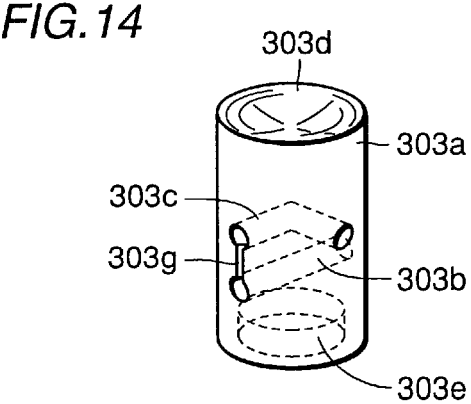
Figure 15:
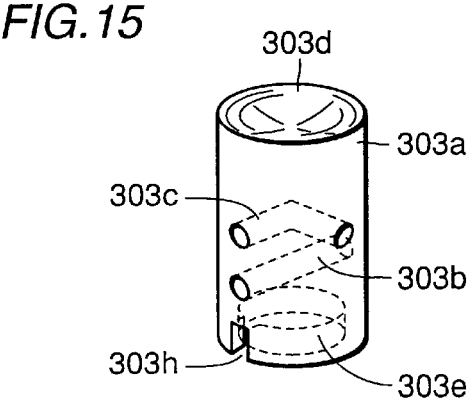

In the first switching button 303a employed for the aforementioned manifold 300, it is preferable to provide a gas port 303g formed by a concave part groove coupling with the first coupling channel 303b and the second coupling channel 303c on a surface of the first switching button 303a, as shown in FIG. 14. When rendering the shape of the first switching button 303a a columnar shape, it is possible to prevent rotation of the first switching button 303a by providing a slit 303h on the first switching button 303a on a lower end portion and providing a convex part (illustration omitted) engaging in this slit 303h on the body part 301 side as shown in FIG. 15. As to the aforementioned gas port and the aforementioned slit, therefore, it is preferable to provide the same also on the second switching button 305a shown in FIG. 4 and the third switching button 307a shown in FIG. 5.

Figure 16:
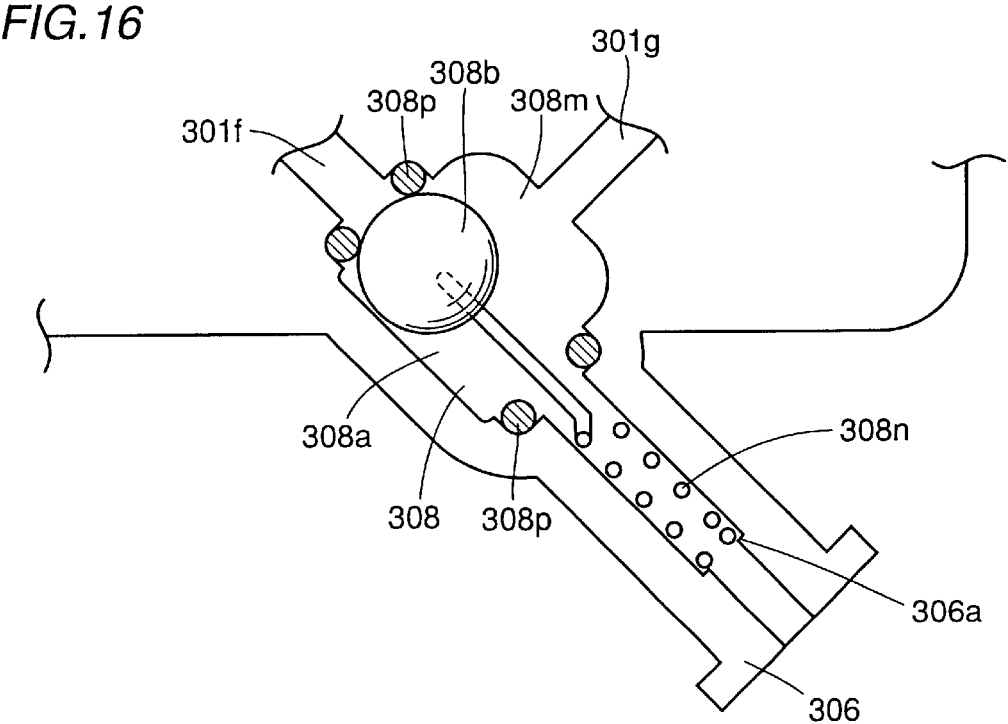
FIG. 16 is a perspective view showing another structure of the fourth channel switching device 308.

In the structure of the fourth channel switching device 308 shown in FIG. 6, the inner diameter of the ball valve chest 308a is provided in a size substantially identical to the outer diameter of the ball valve 308b. When the seventh channel 306 is closed and the pressure of a fluid in the eighth channel 30 if rises, therefore, it may not be possible to completely close the seventh channel 306 with the ball valve 308b due to a fluid remaining in the seventh passage 306 although the ball valve 308b moves toward the seventh channel 306. In such a case, the fluid remaining in the seventh channel 306 is enabled to temporarily flow to the ninth channel by providing a spare room 308m in the ball valve chest 308a as shown in FIG. 16, and it is consequently enabled to completely close the seventh channel 306 with the ball valve 308b. Further, the capacity of the ball valve chest 308a can be reduced by providing the spare room 308, and hence it is enabled to shorten the movement stroke of the ball valve 308b.

As shown in FIG. 16, it is preferable to arrange O-rings 308p consisting of an elastic member such as rubber for ensuring closure of the seventh channel 306 and the eighth channel 301f with the ball valve 308b. In this case, the shape of the fourth coil spring 308n is as shown in the figure.

Figure 17:
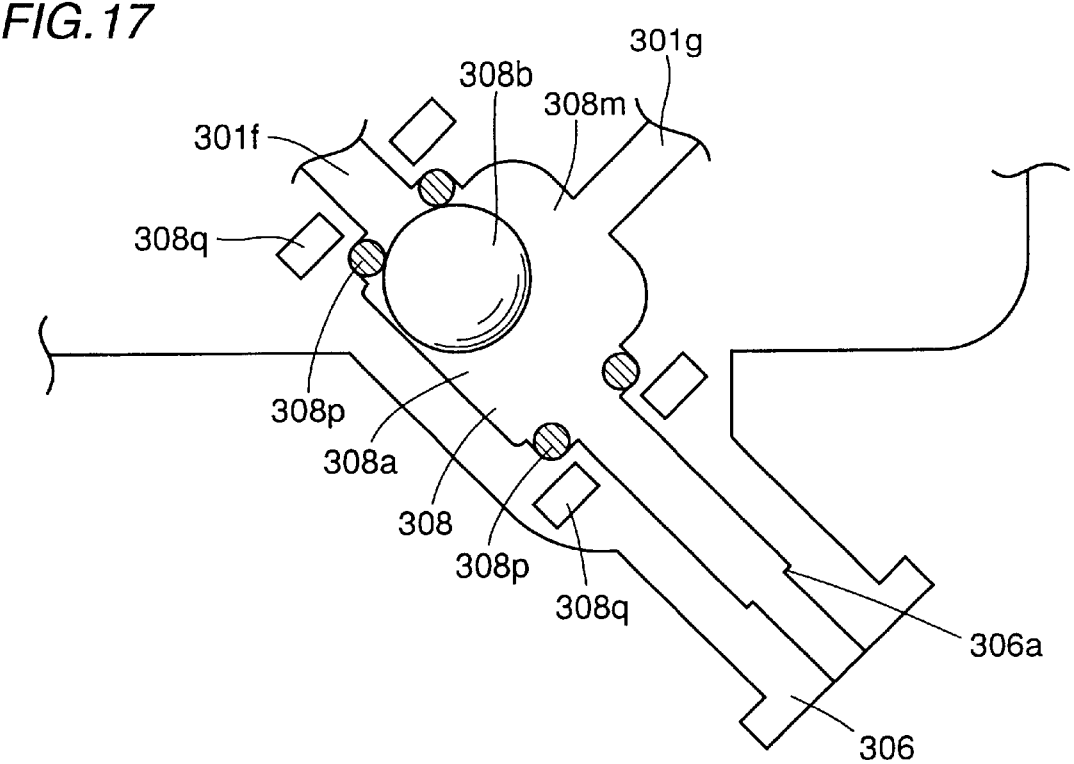
FIG. 17 is a perspective view showing still another structure of the fourth channel switching device 308.

As shown in FIG. 17, further, it is possible to render the fourth coil spring unnecessary by employing a member having magnetism for the ball valve 308b and arranging magnets 308q for attaining aspiration repulsion by magnetic force in the exterior of the ball valve chest 308a. Consequently, obstacles in the channels are reduced and the structure of the fourth channel switching device 308 can be simplified.

It is also possible to employ a structure of making the O-rings 308p also have the action of the magnets 308q and rendering the magnets 308q unnecessary by employing rubber magnets or magnets covered with rubber for the O-rings 308p.

(Embodiment 2)

Figure 18:
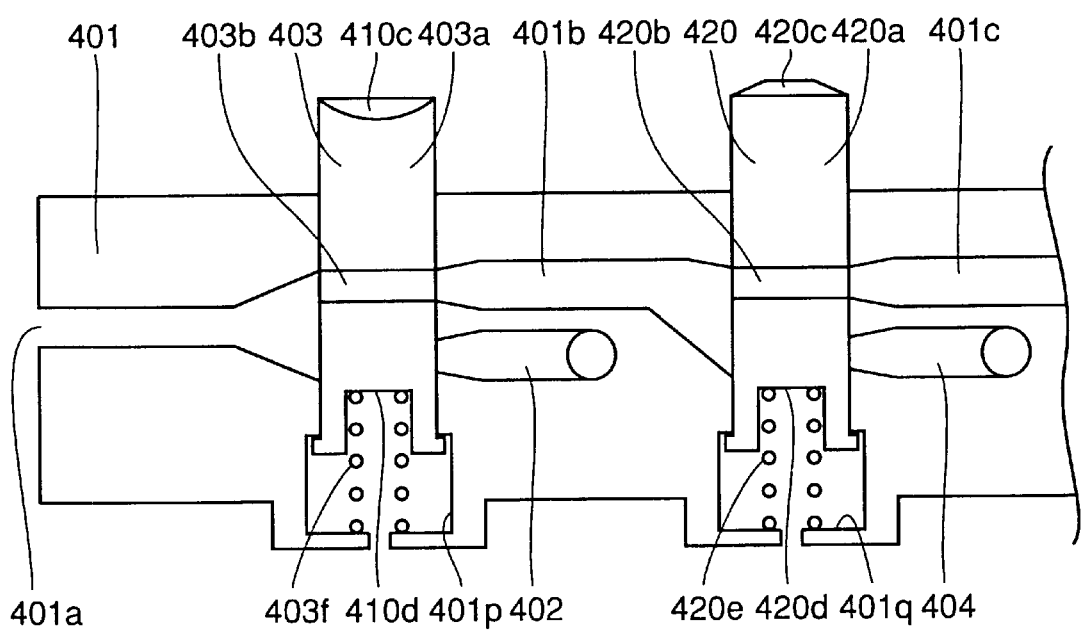
FIG. 18 is a plan view showing the structure of a manifold 400 in an embodiment 2.

FIG. 18 shows the structure of a manifold 400 employing structures as modifications of the first channel switching device 303 and the second channel switching device 305 in the aforementioned embodiment 1. FIG. 18 shows a partial sectional view of a first channel switching device 403 and a second channel switching device 405 of the manifold 400. The structures of a third channel switching device 307 and a fourth channel switching device 308 are identical, and description here is omitted.

Referring to FIG. 18, a body part 401 is provided with a first channel 401a, a second channel 401b, a third channel 402, a fourth channel 401c and a fifth channel 404. As to a sixth channel 301d, a seventh channel 306 and an eighth channel 301f and a ninth channel 301g diverging from the fourth channel 401c, these are similar to the embodiment 1 and description by illustration is omitted.

A first main channel is formed by coupling the first channel 401a and the second channel 40lb with each other. A second main channel is formed by coupling the first channel 401a and the third channel 402 with each other. A first channel switching device 403 for switching the first main channel and the second main channel is provided for the first channel 401a, the second channel 401b and the third channel 402.

A third main channel is formed by coupling the second channel 401b and the fourth channel 401c with each other. A fourth main channel is formed by coupling the second channel 401b and the fifth channel 404 with each other. A second channel switching device 405 for switching the third main channel and the fourth main channel is provided for the second channel 401b, the fourth channel 401c and the fifth channel 404.

As to a third channel switching device 307 for switching a fifth main channel and a sixth main channel and a fourth channel switching device 308 for switching a seventh main channel and an eighth main channel, these are similar to the embodiment 1 and description by illustration is omitted.

Referring to FIG. 18, the first channel switching device 403 has a columnar first switching button 403a having a first coupling channel 403b for coupling the first channel 401a and the second channel 401b with each other on a first position and coupling the first channel 401a and the third channel 402 with each other by sliding in a direction substantially perpendicular to a plane including the first main channel and the second main channel and a first coil spring 403f for urging the first switching button 403a so that the first switching button 403a is urged to be located on the first position in a general state and the first switching button 403a is located on the second position only when moved against urging force.

This first coil spring 403f is arranged between a first concave part 403e provided on the first switching button 403a and a first concave part 401p provided on the body frame 401.

The first switching button 403a is provided with a first recognition concave part 403d for allowing an operator manipulating the manifold 400 to tactually recognize the position of the first switching button 403a.

Such a state that the first switching button 403a is on the first position is referred to as state A1, and such a state that the first switching button 403a is on the second position is referred to as state A2.

The second channel switching device 420 has a second switching button 420a having a fourth coupling channel 420b for coupling the second channel 401b and the fourth channel 401c with each other on a first position and coupling the second channel 401b and the fifth channel 404 with each other on a second position by sliding in a direction substantially perpendicular to a plane including the third main channel and the fourth main channel and a second coil spring 420e for urging the second switching button 420a so that the second switching button 420a is urged to be positioned on the first position in a general state and the second switching button 420a is located on the second position only when moved against urging force.

This second coil spring 420e is arranged between a second concave part 420d provided on the second switching button 420a and a second concave part 401q provided on the body frame 401.

The second switching button 420a is provided with a second recognition convex part 420c for allowing the person manipulating the manifold 400 to tactually recognize the position of the second switching button 420a.

Such a state that the second switching button 420a is on the first position is referred to as state B1, and such a state that the second switching button 420a is on the second position is referred to as state B2.

While members of columnar shapes are employed as the shapes of the aforementioned first switching button 403a and second switching button 420a, the present invention is not necessarily restricted to this shape but any shape is employable so far as the same has a similar function. Further, the first coil spring 403f and the second coil spring 420e are not restricted to the coil springs either but elastic members of any shapes are employable so far as the same have similar functions.

It is enabled to attain function/effect similar to the aforementioned embodiment 1 also in case of using the manifold 400 employing the first channel switching device 403 and the second channel switching device 405 consisting of the aforementioned structures.

While the case of applying the present invention to a manifold employed for angiography has been described as exemplary application of the present invention in each of the aforementioned embodiments, the present invention is not restricted to this exemplary application but is applicable to channel switching of other various fluids.

Therefore, it is to be considered that each of the aforementioned embodiments disclosed this time is illustration and not restrictive in all points. The scope of the present invention is shown not by the above description but the scope of claim for patent, and it is intended that all modifications within the meaning and range equivalent to the scope of claim for patent are included.

What is claimed is:

1. A channel switching apparatus comprising:
   a body frame including a first channel, a second channel, a third channel, a fourth channel, a fifth channel, a sixth channel, a seventh channel, and an eighth channel and a ninth channel diverging from said fourth channel;
   first channel switching means for switching a first main channel formed by coupling said first channel and said second channel with each other and a second main channel formed by coupling said first channel and said third channel with each other;
   second channel switching means for switching a third main channel formed by coupling said second channel and said fourth channel with each other and a fourth main channel formed by coupling said second channel and said fifth channel with each other;
   third channel switching means for switching a fifth main channel formed by coupling said fourth channel and said sixth channel with each other and a sixth main channel formed by coupling said sixth channel and said ninth channel with each other; and
   fourth channel switching means for switching a seventh main channel formed by coupling said seventh channel and said ninth channel with each other and an eighth main channel formed by coupling said eighth channel and said ninth channel with each other, wherein
   said first channel switching means has:
     first switching means provided on an intersection point between said first channel, said second channel and said third channel and having a first coupling channel for coupling said first channel and said second channel with each other on a first position and a second coupling channel for coupling said first channel and said third channel with each other on a second position by sliding in a direction substantially perpendicular to a plane including said first main channel and said second main channel, and
     first urging means for urging said first switching means so that said first switching means is urged to be located on said first position in a general state and said first switching means is located on said second position only when moved against urging force,
   said second channel switching means has:
     second switching means provided on an intersection point between said second channel, said fourth channel and said fifth channel and having a third coupling channel for coupling said second channel and said fourth channel with each other on a first position and a fourth coupling channel for coupling said second channel and said fifth channel with each other on a second position by sliding in a direction substantially perpendicular to a plane including said third main channel and said fourth main channel, and
     second urging means for urging said second switching means so that said second switching means is urged to be located on said first position in a general state and said second switching means is located on said second position only when moved against urging force, said third channel switching means has:
  third switching means provided on an intersection point between said fourth channel, said sixth channel and said ninth channel and having a fifth coupling channel for coupling said sixth channel and said ninth channel with each other on a first position and a sixth coupling channel for coupling said sixth channel and said fourth channel with each other on a second position by sliding in a direction substantially perpendicular to a plane including said fifth main channel and said sixth main channel, and
  third urging means for urging said third switching means so that said third switching means is urged to be located on said first position in a general state and said third switching means is located on said second position only when moved against urging force, and
said fourth channel switching means has:
  fourth switching means provided on an intersection point between said seventh channel, said eighth channel and said ninth channel for sliding between a first position and a second position in a plane including said seventh main channel and said eighth main channel thereby coupling said seventh channel and said ninth channel with each other on said first position and coupling said ninth channel and said eighth channel with each other on said second position, and
  fourth urging means for urging said fourth switching means so that said fourth switching means is urged to be located on said first position in a general state and said fourth switching means is located on said second position against urging force only when the flow rate in said eighth channel exceeds a prescribed value.

2. The channel switching apparatus in accordance with claim 1, wherein said first switching means is a first columnar member extending in the direction substantially perpendicular to the plane including said first main channel and said second main channel, and said first coupling channel and said second coupling channel are provided on its body part with a space in said perpendicular direction,
  a first concave part for storing said urging means is provided on one end of said first columnar member while a first recognition area for allowing a person manipulating the channel switching apparatus to tactually recognize the position of said first switching means is provided on the other end,
  said second switching means is a second columnar member extending in the direction substantially perpendicular to the plane including said third main channel and said fourth main channel, and said third coupling channel and said fourth coupling channel are provided on its body part with a space in said perpendicular direction,
  a second concave part for storing said urging means is provided on one end of said second columnar member while a second recognition area for allowing the person manipulating the channel switching apparatus to tactually recognize the position of said second switching means is provided on the other end,
  said third switching means is a third columnar member extending in the direction substantially perpendicular to the plane including said fifth main channel and said sixth main channel, and said fifth coupling channel and said sixth coupling channel are provided on its body part with a space in said perpendicular direction,
  a third concave part for storing said urging means is provided on one end of said third columnar member while a third recognition area for allowing the person manipulating the channel switching apparatus to tactually recognize the position of said third switching means is provided on the other end, and
  different shapes are provided for said first recognition area, second recognition area and third recognition area respectively.

3. The channel switching apparatus in accordance with claim 1, wherein a syringe having a piston is connected to said first channel and a contrast medium is connected to said third channel in a flowable manner,
  a physiological salt solution is connected to said fifth channel in a flowable manner,
  the other end of a catheter having an end introduced into a blood vessel of a human body is connected to said sixth channel, and
  a sphygmomanometric apparatus is connected to said seventh channel.

* * * * *